United States Patent
Wang et al.

(10) Patent No.: US 9,725,408 B2
(45) Date of Patent: Aug. 8, 2017

(54) RECOVERING UREA AND OIL FROM A UREA/OIL COMPLEX

(71) Applicant: DSM NUTRITIONAL PRODUCTS AG, Wurmisweg, Kaiseraugst (CH)

(72) Inventors: Weijie Wang, Dartmouth (CA); Paul Frederick Mugford, Halifax (CA); Theophilus Cornelus Van Den Heuvel, Dartmouth (CA)

(73) Assignee: DSM Nutritional Products AG, Kaiseraugst (CH)

( * ) Notice: Subject to any disclaimer, the term of this patent is extended or adjusted under 35 U.S.C. 154(b) by 0 days.

(21) Appl. No.: 14/774,870

(22) PCT Filed: Mar. 13, 2014

(86) PCT No.: PCT/IB2014/001035
§ 371 (c)(1),
(2) Date: Sep. 11, 2015

(87) PCT Pub. No.: WO2014/140864
PCT Pub. Date: Sep. 18, 2014

(65) Prior Publication Data
US 2016/0024423 A1    Jan. 28, 2016

(51) Int. Cl.
C07C 273/16    (2006.01)
C11B 3/00    (2006.01)
(Continued)

(52) U.S. Cl.
CPC .......... *C07C 273/16* (2013.01); *C07C 273/02* (2013.01); *C11B 3/006* (2013.01); *C11B 7/0025* (2013.01); *C11B 7/0083* (2013.01)

(58) Field of Classification Search
None
See application file for complete search history.

(56) References Cited

U.S. PATENT DOCUMENTS 2,663,671 A * 12/1953 Wiles et al. ............ C07C 7/152
  208/24
2,734,049 A *  2/1956 Fasce ....................... C07C 7/10
  518/719

(Continued)

FOREIGN PATENT DOCUMENTS

WO    WO 95/11216    *  4/1995
WO    WO9511216        4/1995
WO    WO03089399       10/2003

OTHER PUBLICATIONS

Breivik, H., et al., Productin and quality control of n-3 fatty acids, 1992, Pharmakologie. Clinical Pharmacology, Fish, Fish Oil, W. Zuckschwerdt Verlag, vol. 5, pp. 25-39.*

(Continued)

*Primary Examiner* — Yate K Cutliff
(74) *Attorney, Agent, or Firm* — Shannon McGarrah; Xi Chen

(57) ABSTRACT

Disclosed are methods of recovering urea from a urea/oil complex by drying the complex, combining the complex with water to form a urea solution, and removing water from the urea solution. Methods for recycling the urea in urea complexation processes are also disclosed. Also disclosed are methods of recovering polyunsaturated fatty acids or derivatives thereof from the urea/oil complexes.

17 Claims, 2 Drawing Sheets

(51) Int. Cl.
*C11B 7/00* (2006.01)
*C07C 273/02* (2006.01)

(56) References Cited

U.S. PATENT DOCUMENTS

| | | | | |
|---|---|---|---|---|
| 2,785,151 | A * | 3/1957 | Gorin | C07C 51/487 |
| | | | | 554/106 |
| 4,504,375 | A | 3/1985 | Griffioen | |
| 4,504,376 | A * | 3/1985 | Mead | C10G 73/24 |
| | | | | 208/25 |
| 5,078,920 | A * | 1/1992 | Maza | C11B 3/14 |
| | | | | 549/413 |
| 5,847,209 | A * | 12/1998 | Gupta | C07C 7/152 |
| | | | | 196/14.5 |
| 7,709,668 | B2 * | 5/2010 | Catchpole | C07C 51/48 |
| | | | | 554/184 |
| 2009/0023808 | A1 * | 1/2009 | Raman | A21D 2/16 |
| | | | | 514/549 |
| 2009/0199462 | A1 | 8/2009 | Bist et al. | |
| 2013/0046020 | A1 * | 2/2013 | Liang | C07C 57/03 |
| | | | | 514/560 |

OTHER PUBLICATIONS

Harris, Extending the Cardiovascular Benefits of Omega-3 Fatty Acids, Curr Atheroscler Rep, 2005, 375-38, 7.
Hayes et al., Urea complexation for the rapid, ecologically responsible fractionation of fatty acids from seed oil, JAOCS, 1998, 1403-1409, 75(10.
Holub, Bruce, Clnical Nutrition: 4. Omega-3 Fatty Acids in Cardiovascular Care, JAMC, 2002, 608-15, 166(5).
Kristensen et al., Bioavailability of n-3 fatty acids, Prevention and Treatment in Vascular Disease, 1995, 217-26, (Book).
Marsckner et al., The Story of Urea Complexes, Chem & Eng News, 1955, 494, 33(6).
Okeefe, et al., Omega-3 Fatty Acids: Time for Clinical Implementation, Am. J. Cardiology, 2000, 1239-41, 85.
Radack et al., The Effects of Low Doess of n-3 Fatty Acid Supplementation on Blood Pressure in Hypertensive Subjects, Arch Intern Med, 1991, 1173-80, 151.
Sugano, Michihiro, Balanced Intake of Polyunsaturated Fatty Acids for Health Benefits, J. Oleo Sci., 2001, 305-11, 50(5).

* cited by examiner

RECOVERING UREA AND OIL FROM A UREA/OIL COMPLEX

CROSS REFERENCE TO RELATED APPLICATIONS

This application claims the benefit of the filing date of U.S. Provisional Patent Application No. 61/780,341 filed Mar. 13, 2013, the disclosure of which is hereby incorporated herein by reference.

FIELD

The subject matter disclosed herein generally relates to methods of recovering urea and oil from a urea/oil complex. Also, the subject matter disclosed herein generally relates to methods of recycling the recovered urea.

BACKGROUND

Polyunsaturated fatty acids (PUFAs), including omega-3, omega-6 and omega-9 fatty acids, are vital to everyday life and function. For example, the beneficial effects of omega-3 fatty acids like all-cis-5,8,11,14,17-eicosapentaenoic acid (EPA) and all-cis-4,7,10,13,16,19-docosahexaenoic acid (DHA) on lowering serum triglycerides, preventing cardiac arrhythmias, stabilizing atherosclerotic plaques, reducing platelet aggregation, and reducing blood pressure are well established. See e.g., Dyrberg et al., In: Omega-3 Fatty Acids: Prevention and Treatment of Vascular Disease. Kristensen et al., eds., Bi & Gi Publ., Verona-Springer-Verlag, London, pp. 217-26, 1995; O'Keefe and Harris, *Am J Cardiology* 2000, 85:1239-41; Radack et al., "The effects of low doses of omega-3 fatty acid supplementation on blood pressure in hypertensive subjects: a randomized controlled trial." *Arch Intern Med* 151:1173-80, 1991; Harris, "Extending the cardiovascular benefits of omega-3 fatty acids." *Curr Atheroscler Rep* 7:375-80, 2005; Holub, "Clinical nutrition: 4 omega-3 fatty acids in cardiovascular care," *CMAJ* 166 (5):608-15, 2002. Other benefits of PUFAs are those related to the prevention and/or treatment of inflammation and neurodegenerative diseases, and to improved cognitive development. See e.g., Sugano and Michihiro, "Balanced intake of polyunsaturated fatty acids for health benefits." *J Oleo Sci* 50(5):305-11, 2001.

Sources of beneficial PUFAs include diets rich in PUFAs, nutritional supplementation, or pharmaceutical compositions. These sources typically contain or are derived from marine oils such as fish, but PUFAs can also be derived from microbial sources including various species of *Thraustochytrids*. Plants are also natural sources of PUFAs and have even been modified genetically to include genes that produce various PUFAs in further efforts to reduce costs associated with commercial production of PUFAs.

Oils containing PUFAs usually require at least some level of purification and processing to concentrate the beneficial PUFAs and to remove unwanted components. Processes for purifying or concentrating PUFAs are usually multistep processes that vary depending on the particular product desired. One step that is sometimes performed is known as urea complexation. Urea is known to form complexes with organic compounds having long, straight carbon chains, such as saturated and monounsaturated fatty acids or esters. (See Marschner, "The Story of Urea Complexes," *Chem & Eng News,* 33(6):494-6, 1955; Hayes et al., "Urea Complexation for the Rapid, Ecologically Responsible Fractionation of Fatty Acids from Seed Oil, *JAOCS* 75(10):1403-1409, 1998). Urea forms a complex when combined with the saturated and monounsaturated fatty acids/esters components of the oil, forming what is sometimes called a urea adduct or clathrate. Then, the adduct, including its saturated and monounsaturated fatty acids/esters, is separated from the oil, generally by filtration.

The result of urea complexation is oil with a higher concentration of PUFAs and reduced saturated or monounsaturated fatty acid/ester content. In most processes, the urea adduct is discarded, which is wasteful and inefficient, especially when the adduct can also contain PUFAs in significant amounts. Other processes, such as those disclosed in Hayes et al., focus on recovering residual PUFAs from the adduct and discard the urea.

In light of the health benefits of PUFAs such as omega-3 and omega-6 fatty acids, and the deficiencies with existing methods of urea complexation, it is desirable to find new and cost-effective ways to separate PUFAs from a urea adduct and ways to recycle the urea. The methods disclosed herein address these and other needs.

SUMMARY

In accordance with the purposes of the disclosed materials, compounds, compositions, and methods, as embodied and broadly disclosed herein, the disclosed subject matter, in one aspect, relates to methods of recovering urea and oil (including PUFAs or esters thereof) from a urea/oil complex. In a further aspect, the disclosed subject matter relates to methods of recycling the recovered urea. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects described below.

DETAILED DESCRIPTION

Figure 1:
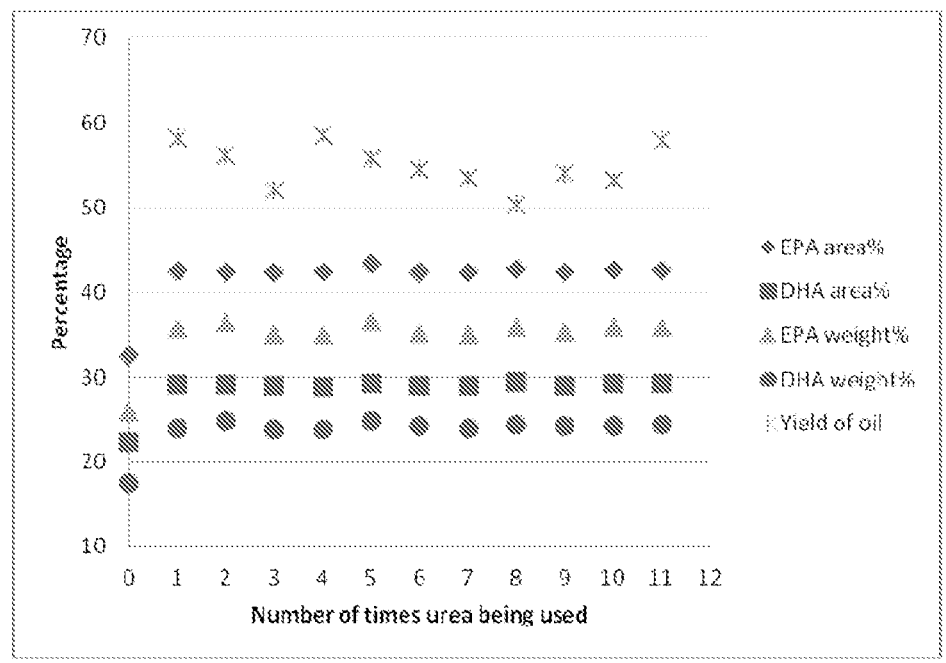
FIG. 1 depicts the EPA and DHA levels of ethyl ester concentrate products and yields of oil in a urea recycle and reuse process. Urea used in each process contained about 90% recycled urea with about 10% fresh urea. The starting EPA and DHA levels for the unused oil are shown at the "0" value on the horizontal axis; the EPA and DHA levels for the urea used once are shown at "1" value on the horizontal axis; and the EPA and DHA levels from 10 cycles of urea recycling and reuse are shown at values "2" through "11", respectively.

The materials, compounds, compositions, and methods described herein can be understood more readily by reference to the following detailed description of specific aspects of the disclosed subject matter and the Examples and Figures included herein.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a complex" includes mixtures of two or more such complexes, reference to "an oil" includes mixtures of two or more such oils, reference to "the polyunsaturated fatty acid" includes mixtures of two or more such polyunsaturated fatty acids, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. "About" can mean within 5% of the stated value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "80" is disclosed, then "about 80" is also disclosed.

References in the specification and concluding claims to parts by weight of a particular element or component in a composition denotes the weight relationship between the element or component and any other elements or components in the composition for which a part by weight is expressed. Thus, in a composition comprising 2 parts by weight of component X and 5 parts by weight component Y, X and Y are present at a weight ratio of 2:5, and are present in such ratio regardless of whether additional components are comprised in the composition.

A weight percent (wt. %) of a component, unless specifically stated to the contrary, is based on the total weight of the formulation or composition in which the component is included.

Reference will now be made in detail to specific aspects of the disclosed materials, compounds, compositions, and methods, examples of which are illustrated in the accompanying Examples and Figures.

Methods and Materials

Disclosed herein are methods of recovering urea and oil from a urea/oil complex. Also, disclosed herein are methods of recycling the recovered urea. The methods of recovering the urea and oil can be performed under acidic conditions or, preferably, without the use of added acid. Further, the methods disclosed herein are cost-effective and efficient through the use of minimal amounts of water and the recovery of many of the reagents used during the process.

Providing a Urea/Oil Complex

The method involves providing a urea/oil complex. The term "urea/oil complex" is used synonymously herein with "urea adduct" or "clathrate." The urea/oil complex can be produced in a commercial or laboratory oil processing step where oils from any of a variety of sources are contacted with urea. Urea preferentially forms a complex with saturated and monounsaturated fatty acids/esters in the oil and is called a urea/oil complex or urea adduct. Thus, the urea/oil complex is a composition containing urea and saturated and/or monounsaturated fatty acids/esters. While the remaining fraction of the oil is rich in PUFAs, some PUFAs can be complexed with the urea and become part of the urea/oil complex. Solvents are also used in this process and so residual solvent is often a part of the urea/oil complex. The disclosed methods thus begin with a urea/oil complex that comprises urea, saturated and monounsaturated fatty acids/esters that are associated with the urea, a residual amount of solvent, and optionally an undesirable residual amount of PUFAs.

Urea

The urea that can be used to form the urea/oil complex can be obtained from a variety of commercial sources. Examples of suitable sources for urea include Acros Organics (Morris Plains, N.J.), Fisher Scientific (Pittsburgh, Pa.), or Sigma Aldrich (St. Louis, Mo.). In some embodiments, the urea in the urea/oil complex is unused urea. In other embodiments, the urea in the urea/oil complex is recycled urea recovered according to the methods described herein. In still other embodiments, the urea can be a mixture of unused and recycled urea. For example, the urea can be a mixture of unused to recycled in a ratio of from 1:10 to 10:1. The urea (unused or recycled) can be substantially pure. In some embodiments, the urea is at least 95% pure. For example, the urea can be at least 96% pure, at least 97% pure, at least 98% pure, at least 99% pure, or can be 100% pure, where any of the stated values can form an upper and/or lower endpoint of a range.

Oils

Oils that are used to form the urea/oil complex comprise one or more PUFAs and saturated and/or monosaturated fatty acids/esters. The purpose of the urea is to complex the saturated and/or monosaturated fatty acids/esters and thereby separate these compounds from the remaining PUFAs. As used herein, "PUFA" refers to a polyunsaturated fatty acid and/or derivative thereof, as well as a mixture of these. Derivatives of PUFAs include alkyl esters (e.g., methyl or ethyl esters), glyceride esters (e.g., mono, di, and triacylglycerol), sterol esters (e.g., cholesterol esters and phytosterol esters), amides, and salts (e.g., sodium, potassium, magnesium, and chromium salts). Mixtures and combinations of various PUFAs are also suitable for use in the methods disclosed herein.

Particularly desirable PUFAs that can be used in the disclosed methods are omega-3 fatty acids. An omega-3 fatty acid is an unsaturated fatty acid that contains as its terminus CH$_3$—CH$_2$—CH=CH—. Generally, an omega-3 fatty acid has the following formula:

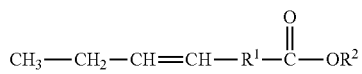

wherein R$^1$ is a C$_3$-C$_{40}$ alkyl or alkenyl group comprising at least one double bond and R$^2$ is H or alkyl group. The term "alkane" or "alkyl" as used herein is a saturated hydrocarbon group (e.g., methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like). The term "alkene" or "alkenyl" as used herein is a hydrocarbon group containing at least one carbon-carbon double bond. Asymmetric structures such as (AB)C=C(CD) are intended to include both the E and Z isomers (cis and trans). In a further example, R$^1$ can be a C$_5$-C$_{38}$, C$_6$-C$_{36}$, C$_8$-C$_{34}$, C$_{10}$-C$_{32}$, C$_{12}$-C$_{30}$, C$_{14}$-C$_{28}$, C$_{16}$-C$_{26}$, or C$_{18}$-C$_{24}$ alkenyl group. In yet another example, the alkenyl group of R$^1$ can have from 2 to 6, from 3 to 6, from 4 to 6, or from 5 to 6 double bonds. Still further, the alkenyl group of R$^1$ can have from 1, 2, 3, 4, 5, or 6 double bonds, where any of the stated values can form an upper or lower endpoint as appropriate. Specific examples of omega-3 fatty acids include, but are not limited to, natural and synthetic, α-linolenic acid (18:3ω3)(ALA), octadecatetraenoic acid (18:4ω3)(stearidonic acid), eicosapentaenoic acid (20:5ω3) (EPA), docosahexaenoic acid (22:6ω3) (DHA), docosapentaenoic acid (22:5ω3) (DPA), eicosatetraenoic acid (24:4ω3), 16:3ω3, 24:5ω3, and/or nisinic acid (24:6ω3); others are noted elsewhere in the specification.

These and other PUFAs, in either their free, esterified, amide, or salt forms, can be found in and obtained from marine oils (e.g., fish oil, seal oil, krill oil), microbial oils (including natural as well as modified microbes whether by way of classical mutagenesis or genetic alteration) such as algal oil (e.g., microalgae oil), fungal oil, as well as plant oil (whether derived from naturally occurring plants or genetically modified plants), among others. Thus these are all suitable oils for use in the disclosed processes.

In a preferred aspect, the methods disclosed herein use oil that comprises DHA and/or EPA, a C$_1$-C$_6$ alkyl ester thereof, a triacylglycerol ester thereof, a cholesterol or phytosterol ester thereof, and amide thereof, a salt thereof, and/or mixtures thereof. Triacylglycerol oils (referred to as TG oils) can be used. But it is preferred that the oil contain PUFAs in their free acid form or, more preferable, their fatty acid alkyl ester form (e.g., fatty acid ethyl or methyl ester).

In specific examples, the oil can comprise a microbial oil, for example, and algal oil (e.g., oil from a dinoflagellate such as *Crypthecodinium cohnii*) or fungal oil (e.g., oil from *Mortiarella Alpina, Thraustochytrium, Schizochytrium,* or a mixture thereof), and/or plant oil, including mixtures thereof.

In specific examples, the oil can comprise a marine oil, such as natural, semi-refined, refined, or concentrated fish oil. Non-alkali treated fish oil is also a suitable oil for use in the disclosed methods. Other marine oils suitable for use herein include, but are not limited to, oil derived from marine mammals and/or marine invertibrates include for example squid oil, octopus oil, krill oil, seal oil, whale oil, and the like, including mixtures and combinations thereof. Any PUFA oil and combination of PUFA oils can be used in the disclosed methods.

The disclosed methods can also be used with vegetable oils such as olive oil, corn oil, palm oil, sunflower oil, flaxseed, and the like.

The PUFAs usable herein can also be crude oils, semi-refined, or refined oils from such sources disclosed herein. Still further, the disclosed methods can use oils comprising re-esterified triacylglycerols. The oil, in some examples, can be bleached, non-deodorized and/or winterized oil.

Urea/Oil Complex

The urea and oil can be combined in the presence of a solvent to form the urea/oil complex. Thus, as a result of the use of solvent in the production of the urea/oil complex, the complex can, and most often does, comprise residual amounts of solvent. In some embodiments, the solvent is an alcohol (e.g., ethanol). Preferably, the solvent is 190 proof ethanol (i.e., 95% ethanol).

In some embodiments, the urea/oil complex is prepared by dissolving urea in ethanol to form a urea/ethanol solution. The ratio of urea to ethanol in the reaction mixture can be from about 1:0.1 to about 1:10, more typically about 1:1.5. To facilitate dissolution of the urea in ethanol, the mixture can be heated. Suitable temperatures to which the ethanol and urea can be mixed include, but are not limited to, from about 60° C. to about 100° C., from about 65° C. to about 95° C., from about 70° C. to about 90° C., or from about 75° C. to about 85° C. For example, the mixture can be heated to from about 85° C. to about 90° C.

The oil can be combined with the urea/ethanol solution at an elevated temperature (i.e., a hot urea/ethanol solution) to form the complex. Optionally, the oil is degassed and/or heated prior to combining the oil with the hot urea/ethanol solution. In some examples, the oil is heated to a temperature within about 15° C. of the hot urea/ethanol solution. For example, when the urea/ethanol solution is at a temperature of about 85° C. to about 90° C., the oil can be heated to a temperature of about 80° C. prior to combining it with the urea/ethanol solution. The oil is mixed with the urea/ethanol solution and the combined mixture is allowed to cool to form the solid urea/oil complex. The same procedures can be used with other solvents.

The ratio of the urea to oil in the reaction mixture can be from about 0.1:1 to about 2:1, more typically about 0.5:1.5, about 0.85:1, or about 1.2:1. The urea/oil complex is then usually separated from the remaining oil, e.g., by filtration.

Solvent Removal

The disclosed methods include the step of taking the urea/oil complex (urea adduct) and removing the residual solvent (e.g., ethanol) to form a dried urea/oil complex (also referred to as a urea "cake"). The dried urea/oil complex is substantially free of solvent. By "substantially free of solvent" is meant that the dried urea/oil complex contains less than about 1 wt. %, less than about 0.5 wt. %, or less than about 0.1 wt. % solvent. The solvent can be removed under vacuum. Suitable temperatures for performing the solvent removal include, but are not limited to, from about 4° C. to about 60° C., preferably from about 10° C. to about 22° C. In other examples, the solvent can be removed at about 5° C., about 10° C., about 15° C., about 20° C., about 25° C., about 30° C., about 35° C., about 40° C., about 45° C., about 50° C., about 55° C., or about 60° C., where any of the stated values can form an upper and/or lower endpoint of a range.

The solvent removal step provides for the recovery of solvent that can be reused in subsequent applications (e.g., subsequent urea/oil complexation reactions). While not wishing to be bound by theory, solvent removal can also improve the recovery of urea and PUFAs from the urea/oil complex. As discussed below, the dried urea/oil complex can be dissolved in water to release the components of the complex. However, it is believed that residual solvents like ethanol stabilize the urea/oil complex from being completely dissolved and instead results in an undesirable oil/urea micro-complex. Thus, by removing residual ethanol according to the methods described herein, the recovery of urea and PUFAs is improved. Without removing the residual solvent, larger amounts of water and/or pH adjustments are needed to achieve separation of oil from the urea. Such pH adjustments (e.g., adding acid), must later be neutralized and affect the purity of the urea after recovery.

Combining with Water

After removing the solvent from the urea/oil complex, the dried urea/oil complex or cake is combined with water. The urea component of the dried urea/oil complex dissolves in the water. This dissolution of urea can be facilitated further at an elevated temperature due, in part, to the increased solubility of urea in water at elevated temperatures. The solubility of urea in water at ambient temperature is about 108 g of urea per 100 mL of water. However, at about 60° C. to about 80° C., the solubility of urea in water increases to about 250-400 grams of urea per 100 mL of water. Thus, in preferred embodiments, the water combining step is performed at temperatures that include, but are not limited to, from about 50° C. to about 80° C., from about 55° C. to about 75° C., or from about 60° C. to about 70° C. In some examples, the dried urea/oil complex can be combined with water at about 50° C., about 55° C., about 60° C., about 65° C., about 70° C., about 75° C., or about 80° C., where any of the stated values can form an upper and/or lower endpoint of a range. In some specific examples, the dried urea/oil complex can be combined with water at about 60° C. to about 80° C., or more specifically, from about 65° C. to about 75° C. or, still more specifically, at about 72° C. Optionally, the water is heated to the elevated temperature and provided to the dried urea/oil complex at the elevated temperature.

Due to the increased solubility of urea in water at elevated temperatures, a minimal amount of water can be used in this step to form an aqueous concentrated urea solution. The total amount of water added will of course depend on how much urea is present in the cake. In some embodiments, the water in the combining step is provided at about 30% by weight to about 50% by weight of the dried urea/oil complex. For example, water can be provided at about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% by weight of the dried urea/oil complex, where any of the stated values can form an upper and/or lower endpoint of a range. In some examples, the water in the combining step is provided at about 40% by weight of the dried urea/oil complex.

It has been found herein that when this step is performed with a dried urea/oil complex, which is substantially free of solvent, the water added to the dried urea/oil complex need not be acidic. Thus, the water can be at a pH of greater than about 6.5, e.g., greater than about 7.0, 7.5, 8.0, 8.5, or 9.0. Typically, the water used can have a pH of from about 7.0 to about 9.0. By not requiring acid, it has been found that the recovered urea contains less impurities (e.g., salts) than if acid had been added. Therefore, the avoidance of acid in the disclosed methods helps to allow the recovered urea to be reused (recycled).

Further, when this step is performed with a dried urea/oil complex, smaller amounts of water can be used to dissolve the urea than would be needed if the residual solvent not been removed. The water added to the dried urea/oil complex results in a high-density, aqueous concentrated urea solution. Thus, the oil component of the dried urea/oil complex, including oil in any oil/urea micro-complexes, will separate from the aqueous concentrated urea solution due to density differences. The expelled oil will form an organic layer above the aqueous layer. This organic layer, which comprises the oil component of the urea/oil complex, can be separated from the aqueous concentrated urea solution.

It is also possible to perform this step repeatedly by, i.e., combining the dried urea/oil complex with water, separating the aqueous layers, and then combining the dried urea/oil complex with water again. Still further, this step can be performed under a nitrogen atmosphere with stirring.

Separating the Urea and the Oil

As noted, combining the dried urea/oil complex with water forms two phases: an aqueous concentrated urea solution, containing the dissolved urea, and an organic phase, containing the oil (saturated and/or monosaturated fatty acids and optionally PUFAs). The two phases can then be allowed to separate further into an aqueous layer and an organic layer. Phase separation can be performed at a temperature from about 50° C. to about 80° C. For example, the separation step can be performed at a temperature of from about 55° C. to about 75° C., or from about 60° C. to about 70° C. In some examples, the two phases can be allowed to separate at about 50° C., about 55° C., about 60° C., about 65° C., about 70° C., about 75° C., or about 80° C., where any of the stated values can form an upper and/or lower endpoint of a range.

Oil can be recovered from the organic phase, sometimes in significant amounts, by washing with water and drying the layer. The urea can be recovered by collecting the aqueous phase (aqueous concentrated urea solution) and evaporating the water to recover the urea.

The urea recovered according to these methods is substantially pure. For example, the urea recovered after evaporating the water can be at least 95% pure, at least 96% pure, at least 97% pure, at least 98% pure, or at least 99% pure. Optionally, the method can further include extracting the aqueous layer with an organic solvent prior to evaporating the water from the aqueous layer.

At least 85% of the urea used in the initial urea/oil complex can be recovered according to the methods described herein. In some embodiments, at least 90% of the urea used in the urea/oil complex can be recovered. For example, about 85%, 86%, 87%, 88%, 89%, 90%, 91%, 92%, 93%, 94%, 95%, 96%, 97%, 98%, or 99% of the urea can be recovered, where any of the stated values can form an upper and/or lower endpoint of a range.

Recycling Urea

The urea recovered according to the methods described herein (referred to as "recovered urea") can be combined with oil and used in subsequent urea/oil complexation steps. Optionally, the amount of urea lost during the process can be supplemented by additional urea. In some examples, the recovered urea is supplemented by 15% or less, 10% or less, or 5% or less additional urea. The urea recovered according to these methods can be recycled ten or more times using the methods described herein. The recovered urea can be broken up before being used in the next complexation process.

EXAMPLES

The following examples are set forth to illustrate the methods and results according to the disclosed subject matter. These examples are not intended to be inclusive of all aspects of the subject matter disclosed herein, but rather to illustrate representative methods and results. These examples are not intended to exclude equivalents and variations which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Certain materials, compounds, compositions, and components disclosed herein can be obtained commercially or readily synthesized using techniques generally known to those of skill in the art. For example, the starting materials and reagents used in preparing the disclosed compositions are either available from commercial suppliers such as Ocean Nutrition Canada Limited (Dartmouth, Canada), Acros Organics (Morris Plains, N.J.), Fisher Scientific (Pittsburgh, Pa.), or Sigma Aldrich (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Example 1

Urea Complexation

Exemplary starting oils and oil blends, processing conditions (oil to urea ratio), and the corresponding products and yields were evaluated for urea complexation. Generally, the complexation was performed by dissolving urea in 95% ethanol at 85-90° C. under reflux. The oil or oil blend was then degassed and heated to 80° C. under nitrogen. The heated oil and the hot urea/ethanol solution were then mixed under nitrogen and allowed to cool while mixing until the temperature was below 40° C. The mixture was stored at 4° C. overnight.

Table 1 lists an exemplary starting oil that could be used for polyunsaturated fatty acid concentrated ethyl ester production, the product yields and EPA and DHA profiles, and the urea processing conditions. The starting oils contained EPA and DHA in their ethyl ester form in their stated weight ratios.

TABLE 1

| Starting oil | Urea Process Oil:Urea:Ethanol | Yield of oil (%) | EPA (%) | DHA (%) | EPA (mg/g) | DHA (mg/g) | Total (mg/g) |
|---|---|---|---|---|---|---|---|
| Starting oil | — | | 30.1 | 23.7 | 251 | 199 | 450 |
| Starting oil | 100:85:127 | 54 | 39.3 | 30.8 | 343 | 262 | 605 |

Example 2

Analysis of Recovered Urea and PUFAs

A urea complex (80 g) was heated to approximately 80° C. in deionized water (80 mL) under a nitrogen atmosphere to give a yellow oil layer and a cloudy aqueous layer. The pH of the water layer changed from 5-6 to 8 during the heating process. The upper yellow oil layer (12.5 g) was removed using a pipette (Oil Layer 1). The pH of the lower layer was adjusted to pH=4 by adding glacial acetic acid. The addition of acid resulted in the separation of a second yellow oil layer, which was also removed (Oil Layer 2). Each oil layer was dissolved in isooctane and washed with warm water three times. The oil layers were analyzed by gas chromatography (Table 2).

TABLE 2

| | EPA (Area Percent) | DHA (Area Percent) |
|---|---|---|
| Oil Layer 1 | 29.8% | 23.8% |
| Oil Layer 2 | 23.7% | 18.6% |

The aqueous layer was divided in half. One half of the cloudy aqueous layer was evaporated to give a white solid and was re-dissolved in water to give a cloudy solution (Aqueous Layer 1). The other half of the cloudy aqueous layer was extracted with ethyl acetate to give a clear, colorless aqueous layer. The water was evaporated to provide a white solid and the solid was re-dissolved to provide a clear solution (Aqueous Layer 2). The ethyl acetate layer contained 0.1 g of ethyl ester as determined by oil class. The purity of the urea was analyzed using combustion analysis and a urea assay. Both tests indicated that the urea recovered from the process after separating the two oil layers was pure. Further, both tests demonstrated that urea obtained after the water evaporation is of similar purity with and without the final organic extraction using ethyl acetate.

Example 3

(Comparative) Urea Recycling via Acid Treatment

Experiments were conducted to recover the urea using heat, water dissolution, and acid treatment. Partial separation occurred upon heating the urea complex to melt the urea and oil (130° C.); however, the separation was not complete and the high temperature damaged the oil. Simply dissolving the complex in water gave some separation, but a significant amount of oil remained complexed to the urea in a cloudy water layer.

Lowering the pH using acid (about 15 mL acetic acid per 100 g urea complex) helped to disrupt the complex to release the remaining oil. The water was evaporated to recover the urea. The recycled urea obtained according to the acid treatment method was used in the complexation process. The recycled urea contained acid residue and possible neutralized compounds, which were somewhat difficult to remove.

The urea recycling process was repeated by adding water (1:1 w/w) to the undried urea/oil complex (without removing ethanol), heating the concentrated solution to 80° C. to separate the layers, and removing the upper oil layer. The cloudy aqueous layer was then acidified to pH about 4 with glacial acetic acid which resulted in two layers, and a second layer of oil was collected. The urea was recovered from the aqueous layer by evaporating the water. The recycled urea from this process was reused in ethyl ester/urea complexation process. The ethyl ester processed by the recycled urea from the acid treatment process had a lower EPA and DHA concentration than the ethyl ester processed with fresh urea (see Table 3).

TABLE 3

| Sample | Yield (%) | EPA (mg/g) | DHA (mg/g) | EPA + DHA (mg/g) |
| --- | --- | --- | --- | --- |
| Starting oil | | 251 | 199 | 450 |
| Product processed with fresh urea | 53.2 | 347 | 263 | 610 |
| Product processed with recycled urea from acid treatment | 53.8 | 332 | 252 | 584 |
| EE blend starting oil | | 259 | 177 | 436 |
| Product processed with fresh urea | 56 | 356 | 243 | 599 |
| Product processed with recycled urea from acid treatment | 56 | 343 | 235 | 568 |

Example 4

Urea Recycling via Solvent Removal

The urea complex from Example 3 dissolved in water, but it was found that after filtration the complex cake from the product processed with recycled urea from the acid treatment contained about 15% ethanol. Thus, ethanol was removed from the complex cake before dissolving it in water to completely disrupt micro-complex without the acid treatment. The resulting ethanol-free complex was able to be dissolved in a minimum amount of water, without acid treatment, to prepare an aqueous concentrated urea solution. The water temperature was varied to determine its impact on process performance (see Table 4). An increased water temperature reduced dissolving time and the amount of water in the recycling process. At 60-80° C., the solubility of urea in water is between 250-400 g/100 mL. Table 4 lists suitable conditions for dissolve the complex. Adding 40% water to the dried complex cake at 72° C. provided especially suitable results.

TABLE 4

| Complex (142 g) after filtration | Water (g) | Temperature (° C.) | Process Performance |
| --- | --- | --- | --- |
| Ethanol stripped complex cake (120 g) | 60 | 65-67 | Longer processing time, higher capacity, but lower temperature, easy handling, |
| | 48 | 70-72 | Quicker processing time, mediate capacity, mediate temperature, easy handling |
| | 36 | 80-85 | Quicker processing time, lower capacity, but higher temperature, higher lost, hard handling |

Example 5

Urea Recycling via Solvent Removal

Figure 3:
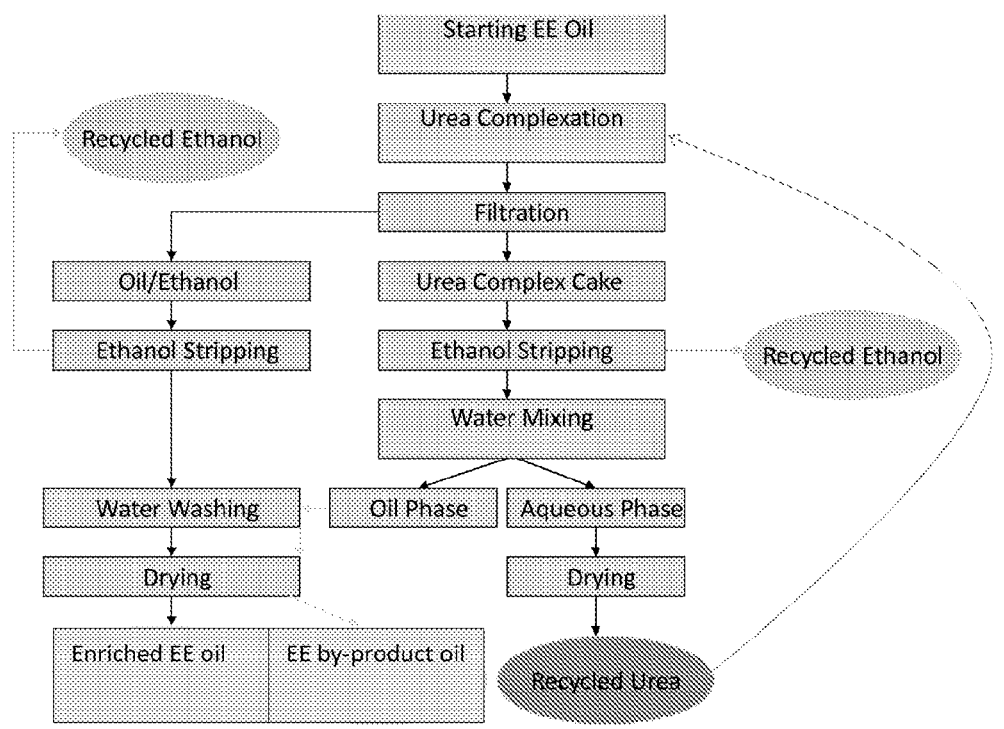
FIG. 3 is a schematic of a urea recycling process chart.

The method described herein requires no acid treatment. Instead, the method includes removing ethanol from the solid complex, which can improve disruption of the oil/urea complex in water solution. The solubility of urea in water at 70° C. is about 300 g/100 mL. Using a small but sufficient amount of water to dissolve urea complex creates an aqueous concentrated urea solution that can expel oil contained in the micro-complex to achieve a pure urea aqueous solution. It also lowers capacity and energy cost, because water used in dissolving urea complex has to be evaporated to recycle urea. The recycled urea from the method described herein showed a good yield (average 91%) and reusability. A procedure for the urea recycle process is provided below. A schematic illustrating exemplary process steps is depicted in FIG. 3.

Urea Recycling

Urea and 95% ethanol were mixed at 85-90° C. under reflux until the urea completely dissolved. Then, ethyl ester starting oil at 80° C. was poured into the urea/ethanol solution while mixing vigorously under nitrogen pressure. Heat was removed and the mixture was continually mixed at room temperature under nitrogen until it cooled to below 40° C. The complex was then cooled to 4° C. The complex was filtered under vacuum to separate the PUFA concentrated ethyl ester from the solid complex. Ethanol was removed and recovered from the ethyl ester concentrates under vacuum at 15-22° C. The resulting oil was washed with warm water to remove urea residue until the resulting oil was clear, and the oil was then dried under vacuum at 60° C. to obtain ethyl ester product. The solid complex was dried under vacuum at 15-22° C. to recover ethanol from the complex cake. Hot water (72-75° C., 40% w/w to dried complex) was used to dissolve urea from the complex and the solution was mixed, using an increasing agitation speed, at 72° C. under a nitrogen atmosphere until no solid remained. The mixture was then settled and the resulting clear oil phase and transparent aqueous phase were separated. After separation, the aqueous phase was dried under vacuum at 60° C. with gentle stirring to recover urea. The recycled urea was mixed with fresh urea to replace the urea lost during the process (on average, 9%) for the next round of urea complexation. The lost urea includes urea that went into the oil/solvent phase after filtration and from normal handling loss during recycling.

Urea Reuse

The ability to repeatedly reuse the recycled urea was confirmed by reusing the recycled urea 10 times. Because each recycling process recovered about 91% of the urea used in complexation, fresh urea (about 9% w/w to total urea) was mixed with recycled urea in each circle to achieve constant production. Testing of recycled urea was conducted by two sets of recycle and reuse experiments. In each set of experiments, urea was recycled and reused for the complexation process 10 times (referred to herein as circles). See Table 5.

TABLE 5

| Circle | Urea recycle information | Recycled urea yield Set 1 (%) | Recycled urea yield Set 2 (%) |
| --- | --- | --- | --- |
| A | Recycled urea from Example 3 | 90.6 | 91.3 |
| B | Recycled urea from A; complex 71.8 g wet, 60.8 g dry, | 91.8 | 90.6 |

TABLE 5-continued

| Circle | Urea recycle information | Recycled urea yield Set 1 (%) | Recycled urea yield Set 2 (%) |
|---|---|---|---|
| C | Recycled urea from B, complex 73.3 g wet, 61.0 g dry, | 91.8 | 90.1 |
| D | Recycled urea from C, complex 66.8 g wet, 58.4 g dry, | 90.6 | 90.0 |
| E | Recycled urea from D, complex 67.4 g wet, 59.1 g dry, | 90.8 | 90.8 |
| F | Recycled urea from E, complex 70.8 g wet, 59.8 g dry, | 90.4 | 92.0 |
| G | Recycled urea from F, complex 70.5 g wet, 60.1 g dry, | 90.8 | 90.1 |
| H | Recycled urea from G, complex 73.6 g wet, 61.3 g dry, | 90.8 | 91.3 |
| I | Recycled urea from H, complex 70.5 g wet, 61.1 g dry, | 92.7 | 90.8 |
|   | Recycled urea from I, complex 74.4 g wet, 61.2 g dry, | 92.0 | 93.2 |

Figure 2:
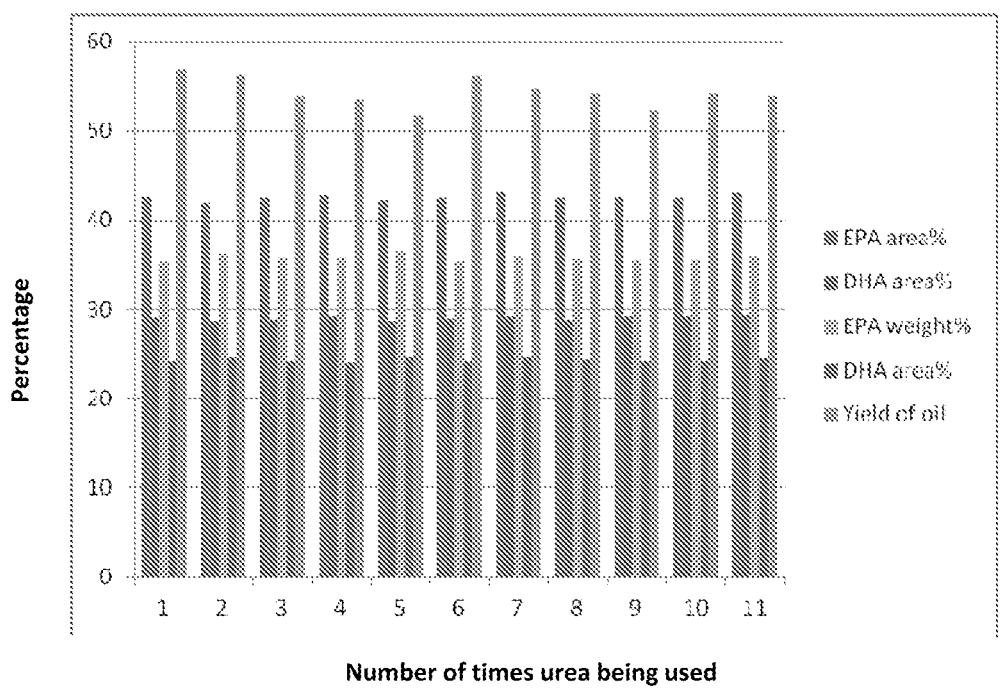
FIG. 2 depicts the EPA and DHA levels of ethyl ether concentrate products and yields of the oil in a urea recycle and reuse process. Urea used in each process contained about 90% recycled urea with about 10% fresh urea. The EPA and DHA levels for the urea used once are shown at "1" value on the horizontal axis; and the EPA and DHA levels from 10 cycles of urea recycling and reuse are shown at values "2" through "11", respectively.

Concentrated ethyl ester products from each circle were analyzed for EPA and DHA levels and product yield. FIGS. 1 and 2 illustrate the results. FIG. 1 shows the EPA and DHA levels of the starting oil (at 0 value of horizontal axis) and the products after urea complexation (at 1 value of the axis) and after consequent 10 times of recycling and reusing process (at 2-11 value of the axis). FIG. 2 depicts the results from the second set of experiments. Consistent PUFA concentrated products were achieved during reusability tests. The slight yield variations were attributed to handling variation during filtration.

During the urea reusability tests, ethanol and lower PUFA ethyl ester by-products were also recovered. Ethanol was recovered from both the liquid phase and the solid complex cake after filtration using vacuum at 4-22° C. Clear ethyl ester by-product was obtained after urea recycling process. Table 6 lists the yields of the recyclables and intermediate products, for this example process.

TABLE 6

| Materials | Weight (g) | Yield (%) |
|---|---|---|
| Starting EE oil | 100 | — |
| Urea used in reaction | 85 | — |
| Ethanol (95%) used in reaction | 127.5 | — |
| EE enriched product | 54.6 | 54.6% (average of 22 reactions) |
| Ethanol recovered from EE concentrate/solvent | 92-100 | ~75% to ethanol used in reaction |
| Complex cake | 142.2 ± 4.0 | — |
| Complex cake after evaporating ethanol | 120.8 ± 2.0 | — |
| Ethanol recovered from complex cake | 21.4 | 16.8% to ethanol used in reaction |
| EE recovered from complex cake | ~40 | ~40% to starting oil |
| Urea recycled from complex cake | 77.4 ± 0.8 | 91% |
| Fresh urea required for next reaction | 7.6 | ~9% needed for next reaction |

The compositions and methods of the appended claims are not limited in scope by the specific compositions and methods described herein, which are intended as illustrations of a few aspects of the claims and any compositions and methods that are functionally equivalent are within the scope of this disclosure. Various modifications of the compositions and methods in addition to those shown and described herein are intended to fall within the scope of the appended claims. Further, while only certain representative compositions, methods, and aspects of these compositions and methods are specifically described, other compositions and methods and combinations of various features of the compositions and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method of recovering urea from a urea/oil complex, comprising:
    a) combining a marine or microbial oil comprising 30% or more of at least one polyunsaturated fatty acid having a carbon chain length of at least 20 with urea in the presence of solvent to form a urea/oil complex and an oil/solvent mixture, wherein the urea:oil ratio is about 0.1:1 to about 2:1, and wherein the oil comprises DHA and/or EPA as a $C_1$-$C_6$ alkyl ester thereof, a triacylglycerol ester thereof, and/or a mixture thereof;
    b) separating the urea/oil complex from the oil/solvent mixture;
    c) removing solvent from the urea/oil complex, thereby forming a dried urea/oil complex that contains less than 1 wt. % solvent;
    d) combining the dried urea/oil complex with water, thereby forming an aqueous concentrated urea solution and an organic phase;
    e) separating the aqueous concentrated urea solution and the organic phase; and
    f) removing water from the aqueous concentrated urea solution, thereby providing a recovered urea.

2. The method of claim 1, further comprising extracting the aqueous concentrated urea solution with an organic solvent prior to step (f).

3. The method of claim 1, wherein after step (e) the method further comprises isolating the organic phase.

4. The method of claim 3, wherein the isolated organic phase is washed with water.

5. The method of claim 1, wherein step (c) is performed under vacuum.

6. The method of claim 1, wherein step (c) is performed at about 4° C. to about 60° C.

7. The method of claim 1, wherein step (c) is performed at about 15° C. to about 22° C.

8. The method of claim 1, wherein the solvent is ethanol.

9. The method of claim 1, wherein water at about 30% by weight to about 50% by weight of the dried urea/oil complex is used in step (d).

10. The method of claim 1, wherein water at about 40% by weight of the dried urea/oil complex is used in step (d).

11. The method of claim 1, where the water in step (d) has a pH of greater than about 6.5.

12. The method of claim 1, wherein the water in step (d) is at about 50° C. to about 80° C.

13. The method of claim 1, wherein step (d) is performed at about 50° C. to about 80° C.

14. The method of claim 1, wherein the oil comprises a fish oil.

15. The method of claim 1, wherein the oil is derived from marine mammals and/or marine invertebrates.

16. The method of claim 1, wherein the microbial oil comprises an algal oil or a fungal oil.

17. A method of recycling urea in a urea/oil complex, comprising:
    a) recovering urea according to the method of claim 1; and
    b) combining oil with the recovered urea.

* * * * *